United States Patent [19]
Dreikorn et al.

[11] 3,953,457
[45] Apr. 27, 1976

[54] AGENT FOR THE CONTROL OF PLANT-PATHOGENIC ORGANISMS

[75] Inventors: Barry A. Dreikorn; Kenneth E. Kramer, both of Indianapolis, Ind.

[73] Assignee: Eli Lilly and Company, Indianapolis, Ind.

[22] Filed: Feb. 15, 1974

[21] Appl. No.: 443,074

Related U.S. Application Data

[60] Division of Ser. No. 275,984, July 28, 1972, Pat. No. 3,839,569, which is a continuation-in-part of Ser. No. 172,317, Aug. 16, 1971, abandoned.

[52] U.S. Cl. ................ 260/288 CF; 260/283 S; 260/283 CN; 260/287 CF; 260/288 R; 424/258
[51] Int. Cl.² .................................... C07D 471/04
[58] Field of Search .................. 260/288 R, 288 CF

[56] References Cited
UNITED STATES PATENTS

| | | | |
|---|---|---|---|
| 2,865,749 | 12/1958 | Van Allan | 260/288 R |
| 2,887,378 | 5/1959 | Williams | 260/288 R |
| 3,758,480 | 9/1973 | Reimlinger et al. | 260/288 R |
| 3,764,681 | 10/1973 | Dreikorn | 260/288 R |
| 3,775,416 | 11/1973 | Reimlinger et al. | 260/288 R |
| 3,775,417 | 11/1973 | De Ruiter et al. | 260/288 R |

*Primary Examiner*—Alton D. Rollins
*Assistant Examiner*—Mary Vaughn
*Attorney, Agent, or Firm*—Kathleen R. S. Page; Everet F. Smith

[57] ABSTRACT

Methods employing and compositions comprising, for the control of plant-pathogenic organisms, specified s-triazolo(4,3-a)quinoline compounds, some of which are claimed as novel compounds.

5 Claims, No Drawings

AGENT FOR THE CONTROL OF PLANT-PATHOGENIC ORGANISMS

CROSS-REFERENCE TO RELATED APPLICATION

This is a division of application Ser. No. 275,984, now U.S. Pat. No. 3,839,569, filed July 28, 1972 which in turn is a continuation-in-part of our copending application Ser. No. 172,311, filed Aug. 16, 1971, now abandoned.

SUMMARY OF THE INVENTION

The present invention is directed to novel methods employing and compositions comprising, for the control of plant-pathogenic organisms, s-triazolo(4,3-a)quinoline compounds of the formulae:

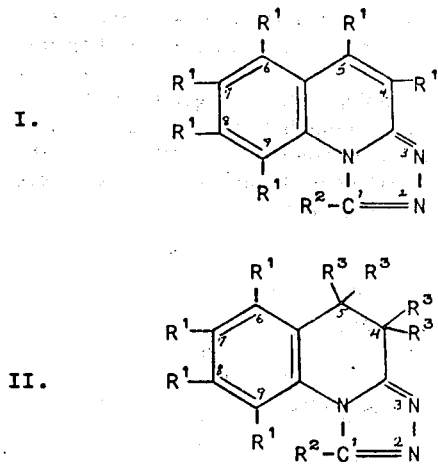

and the phytologically-acceptable mineral acid addition salts thereof, wherein each $R^1$ independently represents hydrogen, halo, loweralkyl of $C_1$–$C_3$, loweralkoxy of $C_1$–$C_3$, formyl, cyano, trifluoromethyl, or substituted methyl of the formula -$CH_2Y$ wherein Y represents amino, loweralkylamino of $C_1$–$C_3$, cyano, hydroxy, halo, or loweralkoxy of $C_1$–$C_3$;

$R^2$ represents hydrogen, loweralkyl of $C_1$–$C_5$, vinyl, cycloalkyl of $C_3$–$C_6$, hydroxy, loweralkoxy of $C_1$–$C_3$, mercapto, loweralkylthio of $C_1$–$C_3$, benzylthio, halo, amino, (loweralkyl of $C_1$–$C_3$)amino, di(loweralkyl of $C_1$–$C_3$)amino, carbamoyl, thiocyanato, acetamido, trifluoromethyl, radical of the formula

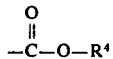

wherein $R^4$ represents sodium, potassium, or loweralkyl of $C_1$–$C_3$, or radical of the formula -$CH_2$-Y' wherein Y' represents amino, loweralkylamino of $C_1$–$C_3$, cyano, halo, loweralkoxy of $C_1$–$C_3$, ((loweralkoxy of $C_1$–$C_2$)methyl), or (halomethyl).

and each $R^3$ independently represents hydrogen, loweralkyl of $C_1$–$C_3$, or halo, subject to the limitation that not more than two $R^3$ groups represent halo or loweralkyl as defined;

the foregoing definitions being subject to the further limitations (1) that in Formula I not more than three of $R^1$ and $R^2$ represent a moiety other than hydrogen; (2) that in Formula II not more than three of $R^1$, $R^2$, and $R^3$ represent a moiety other than hydrogen; and (3) that in both Formulae I and II at least one of $R^2$ and the $R^1$ substituent at the 9-position represents hydrogen.

DETAILED DESCRIPTION OF THE INVENTION - COMPOUNDS

A. Scope

The scope of compounds serving as a fungal control agent in accordance with the present invention is as defined hereinabove. Where the term "halo" is employed, it refers to fluorine, chlorine, bromine, and iodine, only. Those moieties defined herein as loweralkyl (alone or as part of the composite terms loweralkylamino and loweralkylthio) and loweralkoxy can be branched- or straight-chain. Where $R^2$ represents di(loweralkyl of $C_1$–$C_3$)amino, the loweralkyl groups can be the same as or different from one another. In the instance of the salts, the term "phytologically acceptable" is used to designate acids which do not in salt form produce phytotoxicity. The choice of the acid is otherwise not critical, although a given anion may in some instances exhibit special advantages, such as ready solubility, ease of crystallization, and the like. Representative and suitable acids include the following: hydrochloric, hydrobromic, hydriodic, sulfuric, phosphoric, nitric and the like.

B. Synthesis

The compounds to be employed in accordance with the present invention are prepared by a variety of synthetic methods. Several methods, however, are generally applicable.

A first method generally useful in the preparation of the compounds to be employed in accordance with the present invention is the condensation of a 2-hydrazinoquinoline:

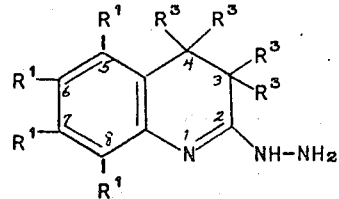

or 3,4-dihydro-2-hydrazinoquinoline:

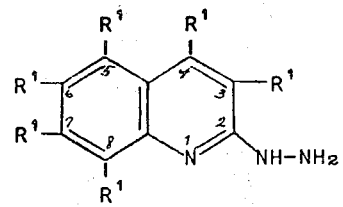

with an acid of the formula $R_2$—COOH or a suitable ester thereof. The reaction is useful for the preparation of compounds wherein $R^2$ represents hydrogen, loweralkyl, cycloalkyl, trifluoromethyl, —$CH_2Y'$ where Y' represents loweralkoxy of $C_1$–$C_3$ or ((loweralkoxymethyl of $C_1$–$C_2$)methyl), or

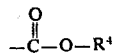

and R[4] represents loweralkyl of $C_1$–$C_3$. Where the identity of R[2] is otherwise, various other synthetic routes, discussed below, are preferred. In general, this synthesis route is useful regardless of the identity of R[1], although where R[1] represents certain of the specified moieties, other synthesis routes may be preferred. Such other routes are discussed below.

To effect this condensation reaction, the reactants are contacted with one another. The reaction consumes the reactants in equimolecular amounts, producing the desired compound and water as by-product. Although an inert solvent can be employed, the acid reactant is typically a liquid and an excess thereof is more conveniently used. The reaction goes forward under a wide range of temperatures, but better yields are more rapidly achieved by conducting the reaction at the reflux temperature of the reaction mixture. Separation, and, if desired, purification, are accomplished in conventional procedures.

A second synthetic method generally applicable to the preparation of the compounds to be employed in accordance with the present invention is the reaction of the same 2-hydrazinoquinoline or 3,4-dihydro-2-hydrazinoquinoline:

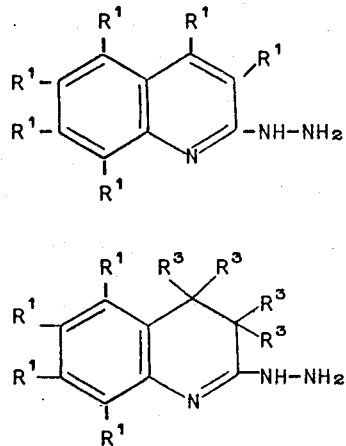

with an ortho ester of the formula

R[2]—C(O—alkyl)$_3$

This specific route is useful for the preparation of those compounds wherein R[2] represents hydrogen, loweralkyl, or cycloalkyl. As in the first synthetic method, the identity of R[1] groups is not critical.

The reaction consumes the reactants in equimolecular amounts, producing the desired compound and the corresponding alkanol as by-product. An inert liquid is conveniently employed as reaction medium. The reaction goes forward under a wide range of temperatures, but better yields are more rapidly achieved by conducting the reaction at the reflux temperature of the reaction mixture. Separation, and, if desired, purification, are carried out in conventional procedures.

In either of the preceding syntheses, the reaction may in some cases produce a 2-(2-acylhydrazino)quinoline or 2-(2-acylhydrazino)-3,4-dihydroquinoline, instead of the desired triazolo product. In such instances, ring closure to the desired product can be achieved by refluxing the intermediate product in a suitable solvent, such as phenol.

Various other synthetic methods are required for those compounds wherein R[2] represents certain moieties. Where R[2] represents -OH or -SH, the compounds are prepared by reacting the same precursor 2-hydrazino compounds described above as starting materials with a phenyl isocyanate or phenyl isothiocyanate. In some instances, the 1-OH and 1-SH compounds exist in equilibrium with the =S and =O forms, i.e.,

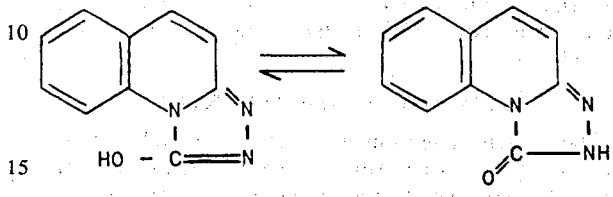

Subsequent alkylation converts the initial products to those compounds wherein R[2] represents loweralkoxy, loweralkylthio, or benzylthio. Compounds wherein R[2] represents amino are prepared by reacting the same 2-hydrazinoquinoline or 3,4-dihydro-2-hydrazinoquinoline with cyanogen bromide.

Yet other compounds to be employed in accordance with the present invention are derived from the condensation product of diethyl oxalate and a precursor 2-hydrazino compound:

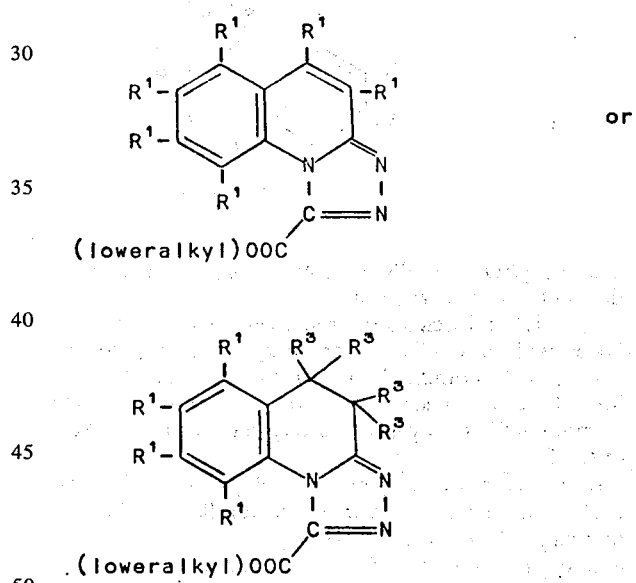

by conventional reactions. Included among such reactions are hydrolysis of the ester to the sodium or potassium salt

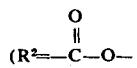

(R[2]=—C—O—sodium or potassium); and aminolysis of the ester to form the amide (R[2]=carbamoyl). Acylation of the 1-NH$_2$ compound yields the acetamido group (R[2]=acetamido) or other amides; and reduction of the amides yields substituted amine groups (R[2]=(loweralkyl of $C_1$–$C_3$)amino or di(loweralkyl of $C_1$–$C_3$)amino.

The R[2] = halo compounds are obtained from compounds wherein R[2] = H, and the thiocyanato derivatives from these halo compounds. The R[2] = H compounds are reacted with a halogenating agent, such as N-halosuccinimide. Other halogen derivatives not readily obtainable by N-halosuccinimide reaction can be obtained by halogen exchange reactions such as the Finklestein Reaction. The thiocyanate group is introduced in conventional procedures such as by reacting a 1-halo compound with an alkali metal thiocyanate. A 1-halo compounds can also be employed as precursors to the 1-substituted amino compounds. In the conduct of these numerous reactions, effecting the identity of the $R^2$ substituents, reference is directed to *Synthetic Organic Chemistry*, Wagner and Zook (John Wiley and Sons, Inc., New York, 1956); and to *Advanced Organic Chemistry*, Fieser and Fieser (Reinhold Publishing Co., New York, 1961).

The $R^2 = -CH_2Y'$ compounds wherein $Y'$ represents amino, loweralkylamino, cyano, halo, or loweralkoxy are prepared by reacting the corresponding methyl-sustituted compounds with N-bromosuccinimide in the presence of a small catalytic amount of benzoyl peroxide. This reaction results in the corresponding bromomethyl compound. The bromine atom of the bromomethyl substituent can then be replaced with other moieties to constitute the other substituted methyl groups. The same bromomethyl substituted compound can also be prepared in an alternate procedure. As discussed above, the $R^2 = -CH_2-Y'$ represents loweralkoxy can be prepared directly in the first general synthetic method described above. These 1-(loweralkoxymethyl) substituted compounds can then be converted to the corresponding 1-(bromomethyl) compounds by procedures known to those skilled in the art.

The $R^2 = -CH_2-Y'$ compounds wherein $Y'$ represents ((loweralkoxy)methyl) are also prepared directly, in the first synthetic method described above. The compounds can then be converted, in conventional procedures, to the corresponding $R^2 = -CH_2-Y'$ compounds wherein $Y'$ represents (halomethyl); subsequent dehydrohalogenation yields the $R^2 =$ vinyl compounds.

The foregoing methods are useful for the preparation of products of Formulae I and II essentially regardless of the identity of the substituents $R^1$ and $R^3$. Generally, it is preferred that substituents of the specified identity already be present on the starting 2-hydrazinoquinoline or 3,4-dihydro-2-hydrazinoquinoline compound. Sometimes, however, it is preferred to conduct the foregoing method with a hydrazino compound bearing a different substituent than that ultimately desired, and then convert the substituent on the resulting triazoloquinoline to the desired substituent. Also, a compound bearing an additional substituent, notably a carboxyl, can be employed and then the carboxyl can be removed by decarboxylation. Such conversions are conducted in accordance with procedures well known to those skilled in the art. Thus, for example, those compounds of the present invention wherein $R^1$ represents substituted methyl are prepared from the corresponding methyl-substituted compound, as described above for the preparation of compounds wherein $R^2$ represents substituted methyl. As discussed above, halogenation of the 1-position, if unsubstituted, can also occur. Mixtures can be separated in conventional procedures, notably column chromatography.

Where $R^1$ represents formyl, the compounds are readily achieved by oxidation of corresponding $-CH_2OH$ compounds; and where $R^1$ represents cyano, by further oxidation to $-COOH$ compounds, amidation to $-CONH_2$ compounds, and subsequent dehydration.

Still other synthetic methods known to those skilled in the art can be used; reference is made to *Synthetic Organic Chemistry*, supra, and to *Advanced Organic Chemistry*, supra.

In addition to the foregoing synthetic methods, certain compounds of Formula II, notably those wherein $R^2$ represents hydroxy, are conveniently prepared by selective reduction of the 4,5-position in the corresponding compounds of Formula I. In carrying out the reaction, the compound of Formula I, conveniently in a suitable liquid as reaction medium, is subjected to hydrogenation in the presence of catalyst, typically a noble metal and preferably palladium or platinum. Suitable liquids include the loweralkanols, ethyl acetate, and the loweralkanoic acids. The catalyst can be employed alone, or —especially in the instance of palladium— can be supported on a carrier such as carbon or an alkaline earth salt. Conveniently, a Parr hydrogenator or other pressure apparatus is used to contain the reaction mixture during hydrogenation, when conducted at superatmospheric pressures. Temperatures of from 20° to 100°C. are operative, but acceptably good results are normally achieved at room temperatures. The reaction consumes the reactants in amounts representing 1 mole of hydrogen per mole of the compound of Formula I, and the reaction is preferably stopped after that amount of hydrogen has been taken up, to limit further non-selective reduction. The desired product is separated from the reaction mixture and from other hydrogenation products by established procedures. Most typically, the reaction mixture is filtered to remove remaining catalyst, and the solvent evaporated to separate the product as a residue. This product residue can be purified, typically by recrystallization.

The compounds defined by Formulae I and II form acid addition salts with mineral acids. These salts are prepared in conventional procedures, by the reaction in a suitable solvent of the compound of Formula I or II as a free base with the desired acid. Separation and, if desired, purification, are carried out by established procedures. Generally, such salts are mono salts. However, certain of the compounds of Formulae I and II— those wherein $R^1$, $R^2$, or $R^3$ is or comprises an amino or substituted amino group—form salts of two acid moieties per moiety of the compound of Formula I or II. Such di salts are also within the scope of the present invention. Also, in the case of dibasic or polybasic acids, salts may exist of two or more molecules of a compound of Formula I or II per molecule of acid. Such di or poly salts are also within the scope of the present invention. In order that the salts be useful in the practice of the present invention, phytologically acceptable salts are preferred.

The following examples illustrate the synthesis of the compounds of the present invention.

EXAMPLE 1:
1-METHYL-s-TRIAZOLO(4,3-a)QUINOLINE

2-Hydrazinoquinoline (5.0 grams) was placed in a 250-milliliter three-necked flask equipped with a mechanical stirrer and a reflux condenser. To this flask was added 100 milliliters of acetic acid. The reaction mixture was refluxed for twelve hours, then allowed to cool; acetic acid was removed by evaporation. The solid which remained consisted of pure 1-methyl-s-triazolo(4,3-a)quinoline. The product was recrystallized from ethanol, m.p., 166°–7°C.

EXAMPLE 2:
1-PROPYL-S-TRIAZOLO(4,3-a)QUINOLINE

2-Hydrazinoquinoline (5.0 grams) was placed in a 250-milliliter three-necked flask equipped with a mechanical stirrer and a reflux condenser. To the flask was added 100 milliliters of n-butanoic acid. The reaction mixture was allowed to reflux overnight. In the morning the reaction mixture was cooled and then made basic by the addition of sodium hydroxide. The desired 1-propyl-s-triazolo(4,3-a)quinoline product was extracted from this solution with methylene chloride and the methylene chloride subsequently stripped off. The product was recrystallized from ethanol, m.p., 158.5°–9.5°C.

EXAMPLE 3: s-TRIAZOLO(4,3-a)QUINOLIN-1-OL

2-Hydrazinoquinoline (15.9 grams; 0.1 mole) was placed in a 250-milliliter three-necked flask equipped with a condenser, along with 70 milliliters of diphenyl ether. To the flask was then added 11.9 grams (0.1 mole) of phenyl isocyanate. The reaction mixture was allowed to reflux for three hours, cooled, and allowed to stand at room temperature overnight. In the morning the precipitate, the desired s-triazolo(4,3-a)quinolin-1-ol product, was filtered off and recrystallized from water. The product so obtained melted at 133.5°–4.5°C.

EXAMPLE 4:
1-METHYLTHIO-s-TRIAZOLO(4,3-a)QUINOLINE s-Triazolo(4,3-a)quinoline-1-thiol was prepared by reacting phenyl isothiocyanate and 2-hydrazinoquinoline in the procedure described in the preceding example.

The s-triazolo(4,3-a)quinoline-1-thiol (10.0 grams) was then placed in a 250-milliliter flask along with an equimolar amount of methyl iodide and an excess of sodium ethoxide in 100 milliliters of ethanol. The reaction mixture was refluxed for 4 hours at which time it was allowed to cool.

Water was added to destroy the sodium ethoxide, and solvent removed by evaporation. The resulting solid was then washed with water and recrystallized from ethanol, yielding the desired 1-methylthio-s-triazolo(4,3-a)quinoline, m.p. 115°–6°C.

EXAMPLE 5:
s-TRIAZOLO(4,3-a)QUINOLINE-1-CARBOXYLIC ACID, SODIUM SALT

Ethyl s-triazolo(4,3-a)quinoline-1-carboxylate was prepared by reacting diethyl oxalate with 2-hydrazinoquinoline, in the manner described in Examples 1 and 2.

The ethyl s-triazolo(4,3-a)quinoline-1-carboxylate (1.0 gram) was placed in 25 milliliters of anhydrous ethanol. The reaction was carried out in a 100-milliliter three-necked flask equipped with a condenser. The flask was heated in order to dissolve the starting material in the ethanol. To this solution was added 20 milliliters of a saturated solution of sodium hydroxide in ethanol. The reaction mixture was allowed to stir for one hour at room temperature after which the precipitate, the desired sodium salt of s-triazolo(4,3-a)-quinoline-1-carboxylic acid, was filtered. The product was boiled in ethanol to remove any starting material. The product so obtained consisted of pure white crystals, m.p., 261°–3°C.

EXAMPLE 6:
1-AMINO-s-TRIAZOLO(4,3-a)QUINOLINE HYDROBROMIDE

2-Hydrazinoquinoline (25.0 grams) was placed in a 3-liter flask (three-necked, equipped with a condenser) containing 1500 milliliters of methanol. To this flask was added 17 grams of cyanogen bromide. The reaction mixture was refluxed for six hours, at which time it was cooled. The reaction mixture was then evaporated down to approximately 200 milliliters. This solution was then poured into 1 liter of absolute ether. The precipitate which formed was washed with an aliphatic naphtha solvent. This precipitate, the desired 1-amino-s-triazolo(4,3-a)quinoline hydrobromide, was separated by filtration.

EXAMPLE 7:
1-AMINO-s-TRIAZOLO(4,3-a)QUINOLINE

The 1-amino-s-triazolo(4,3-a)quinoline hydrobromide obtained as reported in the preceding example was dissolved in water. A sodium acetate/sodium hydroxide mixture was added to break up the salt. The product then precipitated out as the free base, m.p., 250°–3°C.

EXAMPLE 8:
4,5-DIHYDRO-s-TRIAZOLO(4,3-a)QUINOLINE 3,4-Dihydrothiocarbostyril (6.6 grams; 0.04 mole) and 20 milliliters anhydrous hydrazine were mixed and stirred together at room temperature for 0.5 hour. The excess hydrazine was removed by evaporation. A yellow oil remained which IR and NMR indicated was the desired hydrazino derivative. TLC indicated the material was free of impurities. The yellow oil was used directly, without purification, in the next step.

The yellow oil was dissolved in 50 milliliters of 98 percent formic acid, and the stirred solution was refluxed for two hours. The excess formic acid was removed by evaporation, and a brown solid remained. The solid was dissolved in water and an impurity, formyl hydrazide, allowed to crystallize and then removed. The material soluble in water was isolated by removing the water by evaporation and recrystallizing from chloroform the remaining material, the desired 4,5-dihydro-s-triazolo(4,3-a)quinoline. The yield was 2.2 grams, m.p. 164°–5°C.

EXAMPLE 9:
1-METHYL-s-TRIAZOLO(4,3-a)QUINOLINE

To 2-hydrazinoquinoline (15.9 grams; 0.1 mole) in 70 milliliters xylene was added 13.0 grams (0.11 mole) methyl orthoacetate (13.0 grams; 0.11 mole). The stirred solution was refluxed for four hours, during which the methanol that distilled from the reaction was collected. The reaction mixture was cooled overnight, and filtered to separate the desired 1-methyl-s-triazolo(4,3-a)quinoline product. It was recrystallized from 1-butanol, yield, 9.0 grams, m.p., 166°–7°C.

EXAMPLE 10:
1-CHLORO-s-TRIAZOLO(4,3-a)QUINOLINE s-Triazolo(4,3-a)quinoline (10.0 grams; 0.0592 mole) and N-chlorosuccinimide (15.75 grams; 0.1184 mole) were placed in 3.8 liters of carbon tetrachloride in a 5-liter three-necked flask. To the flask was then added a trace of dibenzoyl peroxide. The reaction mixture was refluxed for four hours during which time it was irradiated by means of a UV sun lamp. At the end of four hours, the reaction mixture was allowed to cool. The solid material was then filtered off and the filtrate was stripped down.

The filtrate was placed in ethanol which had been saturated with hydrogen chloride. The material dissolved; however, the 1-chloro-s-triazolo(4,3-a)quinoline formed an insoluble HCl salt which precipitated. This salt was then taken up in water to which sodium bicarbonate was added, to obtain the free base as a white crystalline material, m.p., 162.5°–3.5°C.

EXAMPLE 11:
5-CHLORO-s-TRIAZOLO(4,3-a)QUINOLINE 2,4-Dichloroquinoline (1.0 mole) was combined with 1 mole of anhydrous hydrazine in 4 liters of dioxane. The reaction mixture was heated at reflux for 12 hours at which time the reaction mixture was allowed to cool and the dioxane was stripped off. The resultant solid was refluxed for twelve hours in formic acid, then allowed to cool and the formic acid stripped off. The 5-chloro-s-triazolo(4,3-a)quinoline was then isolated and purified by column chromatography. A silica gel column was used with a 5 percent methanol/95 percent ethyl acetate solution as the eluant. The purified product melted at 242°–3.5°C.

EXAMPLE 12:
1-TRIFLUOROMETHYL-s-TRIAZOLO(4,3-a)QUINOLINE

2-Hydrazinoquinoline (25.0 grams), 50 milliliters of trifluoroacetic acid, and 250 milliliters of xylene were combined in a 500-milliliter three-necked flask equipped with a condenser. The reaction mixture was refluxed overnight. In the morning it was allowed to cool and the solvent was stripped off, yielding 10 grams of a compound determined to be 2-(2-(trifluoroacetyl)hydrazino)quinoline. It was placed in 40 milliliters of phenol and refluxed for 20 hours. The reaction mixture was then steam distilled to remove the phenol, yielding the desired 1-trifluoromethyl-s-triazolo(4,3-a)quinoline product. It was recrystallized from ethanol, m.p., 133.5°–4.5°C.

EXAMPLE 13:
4,5-DIHYDRO-s-TRIAZOLO(4,3-a)QUINOLIN-1-OL s-Triazolo(4,3-a)quinolin-1-ol (2.0 grams) was mixed with 125 milliliters of ethanol, and 1.0 gram of 5 percent palladium on carbon was added. The resulting mixture was hydrogenated at 50 psi hydrogen pressure and a temperature of 50°C., for 6 hours. The mixture was then filtered to remove catalyst, and the filtrate was evaporated to yield the desired 4,5-dihydro-s-triazolo(4,3-a)quinolin-1-ol product, m.p., 181°–2.5°C. Its identity was confirmed by NMR and by microanalysis.

EXAMPLE 14:
1-(2-ETHOXYETHYL)-s-TRIAZOLO(4,3-)QUINOLINE

2-Hydrazinoquinoline (50.0 grams; about 0.3 mole) and 3-ethoxypropionic acid (100 grams; about 0.85 mole) were mixed and refluxed for eight hours. The reaction mixture was then allowed to cool and made basic with 50 percent sodium hydroxide. A precipitate, the desired 1-(2-ethoxyethyl)-s-triazolo(4,3-a)quinoline, formed. It was separated by filtration and recrystallized from ethanol, m.p., 93°C. The identity of the product was confirmed by NMR and by microanalysis.

EXAMPLE 15:
1-VINYL-s-TRIAZOLO(4,3-a)QUINOLINE s-Triazolo(4,3-a)quinoline-1-ethanol hydrochloride salt, prepared by refluxing 1-(2-ethoxyethyl)-s-triazolo(4,3-a)quinoline in concentrated HCl followed by work-up in conventional procedures, was utilized in the subsequent preparation of 1-vinyl-s-triazolo(4,3-a)quinoline via an intermediate, 1-(2-chloroethyl)-s-triazolo(4,3-a)quinoline. More particularly, 2.0 grams of s-triazolo(4,3-a)quinoline-1-ethanol were mixed with 40 milliliters of phosphoryl chloride. The resulting reaction mixture was refluxed for three hours, then allowed to cool and subsequently quenched by slowly pouring it into water, the resulting mixture being maintained at a temperature of 40°–50°C. by addition of ice. The reaction mixture was stirred during the quenching step. The reaction mixture was then made basic by the addition of 50 percent sodium hydroxide and extracted with methylene chloride. A solid, the desired 1-vinyl-s-triazolo(4,3-a)quinoline, remained. It was recrystallized from ethanol, m.p. 117°–7.5°C. NMR, IR, and microanalysis confirmed the identity of the product.

EXAMPLES 16–46:

Other representative compounds, prepared in the methods described and exemplified hereinabove using analogous starting materials, are the following:

5-Methyl-s-triazolo(4,3-a)quinoline-1-thiol, m.p., about 295°C.
9-Chloro-4,5-dihydro-s-triazolo(4,3-a)quinoline, m.p., 212°–3°C.
9-Methyl-s-triazolo(4,3-a)quinoline, m.p., 193°–4°C.
s-Triazolo(4,3-a)quinoline, m.p., 176°–7°C.
1,5-Dimethyl-s-triazolo(4,3-a)quinoline, m.p., 194°–5°C.
5-Methyl-s-triazolo(4,3-a)quinolin-1-ol, m.p., 280°–0.5°C.
7-Methoxy-s-triazolo(4,3-a)quinoline, m.p., 190.5°–1.5°C.
s-Triazolo(4,3-a)quinoline-1-thiol, m.p., 256°–8°C.
9-Chloro-s-triazolo4,3-a)quinoline, m.p., 208°–10°C.
s-Triazolo(4,3-a)quinoline hydrochloride, m.p., 270°C. (d.).
5-Methyl-s-triazolo(4,3-a)quinoline, m.p., 222°–3°C.
1-Ethyl-s-triazolo(4,3-a)quinoline, m.p., 126°–7°C.
9-Fluoro-s-triazolo(4,3-a)quinoline, m.p., 199°–202°C.
9-Ethyl-s-triazolo(4,3-a)quinoline, m.p., 198°–9°C.
5-Chloro-1,4-dimethyl-s-triazolo(4,3-a)quinoline, m.p., 224°–5.5°C.
5-Chloro-4-methyl-s-triazolo(4,3-a)quinoline, m.p., 252°–4°C.
1-Isopropyl-s-triazolo(4,3-)quinoline, m.p., 82°–5°C.

s-Triazolo(4,3-a)quinoline hydriodide, m.p., 235°–40°C. (d.).
1-Methylthio-s-triazolo(4,3-a)quinoline hydriodide, m.p., 195°–200°C. (d).
7-Methoxy-1-methyl-s-triazolo(4,3-a)quinoline, m.p., 146°–7°C.
Ethyl s-triazolo(4,3-a)quinoline-1-carboxylate, m.p., 149°–51°C.
4,5-Dihydro-1-methyl-s-triazolo(4,3-a)quinoline, m.p., 118°–9°C.
1-Cyclopropyl-s-triazolo(4,3-a)quinoline, m.p., 94°–6°C.
1-Acetamido-s-triazolo(4,3-a)quinoline, m.p., 151°–3°C.
1-Ethyl-5-methyl-s-triazolo(4,3-a)quinoline, m.p., 152°–4°C.
1-Butyl-s-triazolo(4,3-a)quinoline, m.p., 115°–7°C.
9-Methyl-4,5-dihydro-s-triazolo(4,3-a)quinoline, m.p., 110°–1°C.
5,7,9-Trimethyl-s-triazolo(4,3-a)quinoline, m.p., 260°–2°C.
5,8-Dimethyl-s-triazolo(4,3-a)quinoline, m.p., 275°–7°C.
1-Ethylthio-s-triazolo(4,3-a)quinoline, m.p., 121°–2°C.
s-Triazolo(4,3-a)quinoline-1-carboxamide, m.p., 230°–2°C.

Other representative compounds to be employed in accordance with the present invention include the following:

1-Methylamino-s-triazolo(4,3-a)quinoline
1-Diethylamino-4,5-dihydro-s-triazolo(4,3-a)quinoline
4,5-Dihydro-1-propylamino-s-triazolo(4,3-a)quinoline
1-Diethylamino-s-triazolo(4,3-a)quinoline
1-Amino-4,5-dihydro-s-triazolo(4,3-a)quinoline
4,5-Dihydro-s-triazolo(4,3-a)quinoline-1-thiol
4,5-Dihydro-1-methoxy-s-triazolo(4,3-a)quinoline
4,5-Dihydro-1-methylthio-s-triazole(4,3-a)quinoline
1-Benzylthio-4,5-dihydro-s-triazolo(4,3-a)quinoline
4,5-Dihydro-1-thiocyanato-s-triazolo(4,3-a)quinoline
1-(Ethoxymethyl)-s-triazolo(4,3-a)quinoline
Potassium 4,5-dihydro-7-methyl-s-triazolo(4,3-a)quinoline-1-carboxylate
1-Bromo-5-methyl-s-triazolo(4,3-a)quinoline
4,5-Dihydro-1-fluoro-s-triazolo(4,3-a)quinoline
1-Iodo-5-methyl-s-triazolo(4,3-a)quinoline
4,5-Dihydro-1,4,5-trichloro-s-triazolo(4,3-a)quinoline
Methyl s-triazolo(4,3-a)quinoline-1-carboxylate
Butyl 4,5-dihydro-s-triazolo(4,3-a)quinoline-1-carboxylate
4,5-Dihydro-1-trifluoromethyl-s-triazolo(4,3-a)quinoline
1-Acetamido-4,5-dihydro-s-triazolo(4,3-a)quinoline
4,5-Dihydro-s-triazolo(4,3-a)quinoline-1-carboxamide
1-Isopropoxy-s-triazolo(4,3-a)quinoline
1-Butyl-4,5-dihydro-s-triazolo(4,3-a)quinoline
1-Cyclopentyl-4,5-dihydro-s-triazolo(4,3-a)quinoline
1-Benzylthio-s-triazolo(4,3-a)quinoline
1-Thiocyanato-s-triazolo(4,3-a)quinoline
4,5-Dichloro- 4,5-dihydro-s-triazolo(4,3-a)quinoline
4,5-Dihydro-7-methoxy-s-triazolo(4,3-a)quinoline
7-Bromo-4,5-dihydro-s-triazolo(4,3-a)quinoline
9-(Methoxymethyl)-4,5-dihydro-s-triazolo(4,3-a)quinoline
4,5-Dihydro-5-ethyl-s-triazolo(4,3-a)quinoline
4,5-Dihydro-9-(ethoxymethyl)-s-triazolo(4,3-a)quinoline
4,5-Dihydro-5,9-dimethyl-s-triazolo(4,3-a)quinoline
1-(Aminomethyl)-s-triazolo(4,3-a)quinoline
1-((Ethylamino)methyl)-s-triazolo(4,3-a)quinoline
1-(Cyanomethyl)-s-triazolo(4,3-)quinoline
1-(Bromomethyl)-s-triazolo(4,3-a)quinoline
1-(Ethoxymethyl)-9-methyl-s-triazolo(4,3-a)quinoline

DETAILED DESCRIPTION OF THE INVENTION: UTILITY

It has been discovered that the compounds of Formulae I and II (hereinafter referred to as "triazoloquinoline compounds") are adapted to be employed for the control of a wide range of plant pathogens, including fungal organisms and bacterial organisms. Thus, the triazoloquinoline compounds can be employed for the control of such organisms as crown gall, rice blast, powdery mildew, anthracnose, and the like. The compounds are particularly suited for the control of fungal organisms, and give particularly good results in the control of rice blast.

The compounds can be employed and are effective when utilized in any number of embodiments. In accordance with prevalent practice, the compounds can be applied, and are effective against plant-pathogenic organisms when applied, to the foliage of plants susceptible to attack. In addition, the triazoloquinoline compounds can be applied to seeds to protect the seeds and ensuing plants from the attack of plant-pathogenic organisms. Also, the compounds can be distributed in soil to control plant-pathogenic organisms. It has been found that many of the compounds are translocated through plants, so that in this last embodiment, control is achieved of foliage-attacking organisms as well as organisms which attack other plant parts.

Most broadly, the method of the present invention for the control of plant-pathogenic organisms comprises applying to a locus of the organisms an effective amount of one or more of the triazoloquinoline compounds. The triazoloquinoline compounds can be used alone; but the present invention also embraces the employment of a liquid, powder, or dust composition containing one or more of the triazoloquinoline compounds. Such compositions are adapted to be applied to living plants without substantial injury to the plants. In preparing such compositions, the triazoloquinoline compounds can be modified with one or more of a plurality of additaments including organic solvents, petroleum distillates, water or other liquid carriers, surface active dispersing agents, and finely divided inert solids. In such compositions, the triazoloquinoline compound can be present in a concentration from about 2 to 98 percent by weight. Depending upon the concentration in the composition of the triazoloquinoline compound, such augmented compositions are adapted to be employed for the control of undesirable plant pathogens or employed as concentrates and subsequently diluted with additional inert carrier to produce the ultimate treating compositions. Preferred compositions are those comprising both a finely divided solid and a surface active agent.

The exact concentration of the triazoloquinoline compound employed in the composition for application to plantpathogens and/or their habitats can vary provided an effective amount is applied either on the organism or its environment. The amount which is effective is dependent in part upon the susceptibility of the particular plant pathogen and upon the activity of the compound employed. In general, good results are obtained with liquid compositions containing from about 0.001 to 0.1 percent or more by weight of triazoloquinoline compound. With dusts, good results are usually obtained with compositions containing from 0.5 to 5.0 percent or more by weight of traizoloquinoline compound. In terms of acreage application, good controls of plant pathogens are obtained when the triazoloquinoline compounds are applied to plots of growing plants at a dosage of from 0.5 to 5.0 or more pounds per acre.

In the preparation of dust compositions, triazoloquinoline compounds can be compounded with any of the finely divided solids such as pyrophyllite, talc, chalk, gypsum, and the like. In such operations, the finely divided carrier is ground or mixed with the triazoloquinoline compound or wet with a solution of the same in a volatile organic solvent. Similarly, dust compositions containing the products can be compounded with various solid surface active dispersing agents such as fuller's earth, bentonite, attapulgite, and other clays. Depending upon the proportions of ingredients, these dust compositions can be employed for the control of plant pahogens or employed as concentrates and subsequently diluted with an additional solid surface active dispersing agent or with pyrophyllite, chalk, talc, gypsum, and the like to obtain the desired amount of active ingredient in a composition adapted to be employed for the control of plant pathogens. Also, such dust compositions, when employed as concentrates, can be dispersed in water, with or without the aid of dispersing agents, to form spray mixtures.

Further, the triazoloquinoline compounds or a liquid or dust concentrate compositon containing such compounds can be incorporated in intimate mixture with surface active dispersing agents such as non-ionic emulsifying agents to form spray compositions. Such compositions are readily employed for the control of plant-pathogens or can be dispersed in liquid carriers to form diluted sprays containing the toxicants in any desired amount. The choice of dispersing agents and amounts thereof employed are determined by the ability of the agents to facilitate the dispersion of the concentrate in the liquid carrier to produce the desired spray compositions.

Similarly, the triazoloquinoline compounds can be compounded with a suitable water-immiscible organic liquid and a surface active dispersing agent to produce emulsifiable concentrates which can be futher diluted with water and oil to form spray mixtures in the form of oil-water emulsions. In such compositions, the carrier comprises an aqueous emulsion, i.e., a mixture of water-immiscible solvent, emulsifying agent and water. Preferred dispersing agents which can be employed in these compositions are oil-soluble and include the non-ionic emulsifiers such as condensation products of alkylene oxides with the inorganic acids, polyoxyethylene derivatives of sorbitan esters, complex ether alcohols and the like. Suitable organic liquids which can be employed in the composition include petroleum oils and distillates toluene, and synthetic organic oils. The surface active dispersing agents are usually employed in liquid compositions in the amount of from 0..1 to 20.0 percent by weight of the combined weight of the dispersing agent and active compound.

When operating in accordance with the present invention, the triazoloquinoline compounds or a composition containing the compounds can be applied to the pathogen to be controlled, or to their habitats in any convenient fashion, e.g., by means of hand dusters or sprayers. Applications to the above-ground portions of plants conveniently can be carried out with power dusters, boom sprayers, high-pressure sprayers, and spray dusters. In large-scale operations, dusts or low-volume sprays can be applied from airplanes. In the use of the triazoloquinoline compounds for the control of rice blast, specialized modes of application may be preferred, owing to the peculiar cultural conditions under which rice is grown. Such specialized methods include surface water application, soak treatment of plants to be transplanted, seed treatment, and the like; other methods will be obvious to those skilled in the art.

The following examples illustrate the utility of the triazoloquinoline compounds for the control of plant pathogens and will enable those skilled in the art to practice the same.

EXAMPLES 47–61:

Various of the triazoloquinoline compounds to be employed in accordance with the present invention are evaluated for the control of *Colletotrichum lagenarium* (anthracnose) on cucumber. These evaluations were conducted in accordance with the following procedure.

In each individual evaluation, a 4-inch pot containing sterilized soil, with a layer of vermiculite on the surface, was seeded with four cucumber seeds and held under normal greenhouse conditions. The seedlings were thinned to two plants; about fifteen days after the seeding, the foliage was sprayed with a solution of the respective triazoloquinoline compound, permitted to dry, and then inoculated by spraying it with a water suspension of conidia of *Colletotrichum lagenarium*.

Each triazoloquinoline was formulated in conventional procedues. Typically, the compound was dispersed in a specified amount of cyclohexanone containing a small amount of a blend of two sulfonate-nonionic surfactants, and then diluted with water to obtain an ultimate treating composition containing 400 parts of the given compound per million parts by weight of the ultimate composition, in addition to the cyclohexanone in a concentration of 0.67 percent and the surfactant blend in a concentration of 0.0353 percent.

The suspension of conidia was prepared by culturing the fungus in petri plates on orange juice agar at 22°C. for fourteen days. The plates were then flooded with distilled water and the surface scraped. The resulting aqueous suspension from four plates were filtered through cheesecloth, brought up to a volume of 50 milliliters, and used for spraying plants in about 35 pots.

After the plants had been inoculated, they were placed in a moist chamber at 18°C. for forty-eight hours, then removed and held for about nine days under normal greenhouse conditions, and then evaluated for control of anthracnose.

In each evaluation, there was a control, based on treatment by an aqueous control solution containing cyclohexanone and the surfactant blend in the same respective concentrations.

The results of the evaluations were as set forth in the following table, using the following disease rating system:
1—severe
2—moderatley severe
3—moderate
4—slight
5—no disease In the control pots, there was uniformly a heavy infestation of anthracnose on the cucumber plants. Phytotoxicity was uniformly non-existent or only slight in degree. Where more than one evaluation of the same compound was conducted, an average is reported in the table.

TABLE 1:

CONTROL OF ANTHRACNOSE

| Compound | Disease Rating |
|---|---|
| 9-Chloro-4,5-dihydro-s-triazolo(4,3-a)quinoline | 5 |
| 9-Methyl-s-triazolo(4,3-a)quinoline | 4+ |
| 1,5-Dimethyl-s-triazolo(4,3-a)quinoline | 4+ |
| 5-Methyl-s-triazolo(4,3-a)quinolin-1-ol | 3– |
| 4,5-Dihydro-s-triazolo(4,3-a)quinoline | 4+ |
| 5-Methyl-s-triazolo(4,3-a)quinoline | 3– |
| s-Triazolo(4,3-a)quinolin-1-ol | 4+ |
| 1-Methyl-s-triazolo(4,3-a)quinoline | 5 |
| 1-Ethyl-s-triazolo(4,3-a)quinoline | 3+ |
| 1-Trifluoromethyl-s-triazolo(4,3-a)quinoline | 3 |
| Ethyl s-triazolo(4,3-a)quinoline-1-carboxylate | 4+ |
| 4,5-Dihydro-1-methyl-s-triazolo(4,3-a)quinoline | 3 |
| 1-Chlorotriazolo(4,3-a)quinoline | 4+ |
| 5-Chloro-s-triazolo(4,3-a)quinoline | 5 |
| 1-Vinyl-s-triazolo(4,3-a)quinoline | 3– |

EXAMPLES 62–74:

Representative triazoloquinoline compounds were also evaluated for the control of the causative pathogen of crown gall disease (*Agrobacterium tumefaciens*) on tomato plants. Each such evaluation was conducted in accordance with the following procedure.

Three tomato seeds were planted in sand in 4-inch plastic pots, and later thinned to two plants. Meanwhile, an inoculum of *Agrobacterium tumefaciens* was grown in test tubes on homemade potato dextrose agar. The cultures were then flooded with sterile water to make the required amount of bacterial suspensions, which was used to inoculate the tomato seedlings at about four weeks following seeding. The inoculation was carried out by dipping a small insect mounting needle into the bacterial suspension and then passing the needle through the stem of each tomato plant. The plants were then removed from the sand and the roots of each placed in an aqueous solution in a large test tube, the solution containing the test chemical in a concentration of 40 ppm., 0.067 percent cyclohexanone, and 0.00353 percent surfactant, and sodium chloride in a concentration of 0.85 percent. The plants were held under normal greenhouse conditions, with daily aeration, for about 10 days. At this time, each plant was observed to determine the presence of crown gall disease.

A control was conducted by placing two inoculated plants in a solution in a separate test tube, which solution contained all ingredients except test chemical. This test tube was held and treated in all other respects exactly like the tubes containing the treated plants.

The results of the evaluations are presented in the following table, employing the same rating scales as in previous examples. All control plants showed extensive symptoms of crown gall disease. Phytotoxicity was in all instances either non-existent or of only slight degree, except that moderate phytotoxicity was noted in the case of 1-ethyl-s-triazolo(4,3-a)quinoline; 1-methylthio-s-triazolo(4,3-a)quinoline; and 1-propyl-s-triazolo(4,3-a)quinoline.

TABLE 2:

CONTROL OF CROWN GALL

| Compound | Disease Rating |
|---|---|
| Sodium s-triazolo(4,3-a)quinoline-1-carboxylate | 3 |
| 1-Methylthio-s-triazolo(4,3-a)quinoline | 5 |
| 9-Methyl-s-triazolo(4,3-a)quinoline | 5 |
| s-Triazolo(4,3-a)quinoline | 5 |
| 1,5-Dimethyl-s-triazolo(4,3-a)quinoline | 3 |
| 7-Methoxy-s-triazolo(4,3-a)quinoline | 5 |
| s-Triazolo(4,3-a)quinolin-1-ol | 5 |
| 1-Methyl-s-triazolo(4,3-a)quinoline | 5 |
| 1-Ethyl-s-triazolo(4,3-a)quinoline | 5 |
| 7-Methoxy-1-methyl-s-triazolo(4,3-a)quinoline | 3 |
| 1-Propyl-s-triazolo(4,3-a)quinoline | 5 |
| 1-Trifluoromethyl-s-triazolo(4,3-a)quinoline | 5 |
| Ethyl s-triazolo(4,3-a)quinoline-1-carboxylate | 5 |

EXAMPLES 75–77:

Various of the present triazoloquinoline compounds were evaluated for the control of powdery mildew (*Erysiphe polygoni*) on beans. The evaluations were conducted as follows.

In 4-inch pots of soil, four bean seeds were planted, and later thinned to two seedlings. On the tenth day following seeding, a test chemical was applied to the young plants in the form of a composition formulated as described hereinabove in Examples 47–61 and containing 400 parts of chemical per million parts of ultimate composition by weight. The treated plants were then placed near to and beneath other plants heavily infested with powdery mildew, to assure infestation of the treated plants by natural air currents. In this relationship, the plants were held under normal greenhouse conditions for about seven to ten days, at which time the plants were observed to determine the presence of symptoms of powdery mildew disease. A control was run with each evaluation; the control consisted of a group of four plants treated with a solvent-emulsifier solution containing no test chemical, also as described in Examples 47–61. The results are as set forth in the following table, employing the same rating scales as in previous examples. In the controls, the bean plants uniformly showed heavy infestation by powdery mildew. No phytotoxicity was observed on any of the groups of plants.

TABLE 3:

CONTROL OF POWDERY MILDEW

| Compound | Disease Rating |
|---|---|
| 1-Methylthio-s-triazolo(4,3-a)quinoline | 3 |
| 1-Propyl-s-triazolo(4,3-a)quinoline | 3– |
| 1-Chlorotriazolo(4,3-a)quinoline | 3– |

EXAMPLES 78-116:

Various triazoloquinolines were evaluated for the control of rice blast (*Piricularia oryzae*). The evaluation was carried out in accordance with the following procedure: a soil was prepared by blending together equal parts of masonry sand and shredded top-soil. The soil was placed in 4-inch pots and thickly seeded with rice seed. The seeded pots were then held under typical greenhouse conditions for about 2 weeks, by which time there were thick stands of rice seedlings in each pot.

Also, an aqueous suspension of conidia of the rice blast fungus was prepared. The fungus was cultured in petri dishes on rice polish agar at 28°C. After 8 days, each plate was flooded with 20 milliliters of distilled water and the culture surface was scraped with a rubber policeman to separate conidia.

In each instance, a treating solution prepared as described in Examples 47–61 was sprayed onto the leaf surfaces of the rice stand in one pot, allowed to dry, and the foliage then inoculated with the aqueous suspension of conidia of the rice blast organism. In each instance, the treating solution contained 400 parts of the compound per million parts of ultimate solution, by weight. The pot was placed in a moist chamber at 18°C. and held there for 40 hours, then returned to the greenhouse and held under typical greenhouse conditions for 6 days. At this time, readings were made in accordance with the same disease rating scale reported in preceding examples. The control was conducted as follows: Pots of rice seedlings were sprayed with an aqueous solution of cyclohexanone and the same blend of two sulfonate-nonionic surfactants but containing no compound. Otherwise, the pots were treated identically.

The results of the evaluations are as reported in the following table. Not all of these evaluations were conducted simultaneously. In all tests, however, the untreated control pots showed extensive symptoms of rice blast. Generally, no phytotoxicity was observed; however, on a few of the treated pots, there was slight phytotoxicity.

TABLE 4:

CONTROL OF RICE BLAST

| Compound | Disease Rating |
|---|---|
| Sodium s-triazolo(4,3-a)quinoline-1-carboxylate | 3– |
| 1-Methylthio-s-triazolo(4,3-a)quinoline | 4+ |
| 9-Chloro-4,5-dihydro-s-triazolo(4,3-a)quinoline | 5 |
| 9-Methyl-s-triazolo(4,3-a)quinoline | 5 |
| s-Triazolo(4,3-a)quinoline | 4+ |
| 1,5-Dimethyl-s-triazolo(4,3-a)quinoline | 3 |
| 5-Methyl-s-triazolo(4,3-a)quinolin-1-ol | 3– |
| 7-Methoxy-s-triazolo(4,3-a)quinoline | 4– |
| 4,5-Dihydro-s-triazolo(4,3-a)quinoline | 5 |
| s-Triazolo(4,3-a)quinoline-1-thiol | 3 |
| 5-Methyl-s-triazolo(4,3-a)quinoline | 4 |
| s-Triazolo(4,3-a)quinolin-1-ol | 5 |
| 1-Methyl-s-triazolo(4,3-a)quinoline | 5 |
| 1-Ethyl-s-triazolo(4,3-a)quinoline | 3+ |
| s-Triazolo(4,3-a)quinoline hydriodide | 4+ |
| 7-Methoxy-1-methyl-s-triazolo(4,3-a)quinoline | 4– |
| 1-Propyl-s-triazolo(4,3-a)quinoline | 3– |
| 1-Trifluoromethyl-s-triazolo(4,3-a)quinoline | 4– |
| Ethyl s-triazolo(4,3-a)quinoline-1-carboxylate | 3– |
| 4,5-Dihydro-1-methyl-s-triazolo(4,3-a)quinoline | 5 |
| 1-Amino-s-triazolo(4,3-a)quinoline | 4 |
| 1-Cyclopropyl-s-triazolo(4,3-a)quinoline | 3 |
| 1-Butyl-s-triazolo(4,3-a)quinoline | 4 |
| 4,5-Dihydro-9-methyl-s-triazolo(4,3-a)quinoline | 4+ |
| 5,7,9-Trimethyl-s-triazolo(4,3-a)quinoline | 3 |
| 5-Chloro-s-triazolo(4,3-a)quinoline | 4+ |
| 1-(2-Ethoxyethyl)-s-triazolo(4,3-a)quinoline | 3 |
| 1-Chloro-s-triazolo(4,3-a)quinoline | 5 |
| 1-(Ethoxymethyl)-s-triazolo(4,3-a)quinoline | 3 |
| 1-Vinyl-s-triazolo(4,3-a)quinoline | 3+ |
| s-triazolo(4,3-a)quinoline hydrochloride | 3– |
| 9-Fluoro-s-triazolo(4,3-a)quinoline | 4+ |
| 9-Ethyl-s-triazolo(4,3-a)quinoline | 4– |
| 5-Chloro-1,4-dimethyl-s-triazolo(4,3-a)quinoline | 3+ |
| 4-Chloro-5-methyl-s-triazolo(4,3-a)quinoline | 5 |
| 1-Isopropyl-s-triazolo(4,3-a)quinoline | 3 |
| 1-Ethylthio-s-triazolo(4,3-a)quinoline | 4– |
| 1-Ethyl-5-methyl-s-triazolo(4,3-a)quinoline | 4 |
| 9-Chloro-s-triazolo(4,3-a)quinoline | 5 |

EXAMPLES 117-120:

Certain of the triazoloquinoline compounds to be employed in accordance with the present invention were also evaluated for control of rice blast when applied to the soil prior to planting. In these evaluations, a quantity of the respective compound was dissolved in ethanol, the solution sprayed with a DeVilbiss atomizer onto soil rotating in a drum, and the soil thus treated placed in 4-inch round pots having no drainage holes. The procedures were such as to constitute a specified number of pounds of the triazoloquinoline compound per acre—25 and 12.5 pounds per acre. The pots were then seeded to rice (variety, Nato) and held under typical greenhouse conditions for 2 weeks, at which time the rice seedlings were inoculated with conidia of *Piricularia oryzae*, the preparation and inoculation as described in the preceding examples, and held in a moist chamber at 18°C. for 48 The hours. The were then removed and again held under greenhouse conditions for another 5 days. At this time, observations for disease severity were made; results are as reported below using the rating scale of preceding examples.

There were three replications per test and additionally a control utilizing soil treated only with an aqueous solution of the same concentration of ethanol. In the control plots, there were extensive symptoms of rice blast disease.

TABLE 5:

CONTROL OF RICE BLAST, PRE-PLANT SOIL INCORPORATED APPLICATION

| Compound | Rate of Application of Compound in Pounds per Acre | Disease Rating |
|---|---|---|
| 4,5-Dihydro-s-triazolo(4,3-a)quinoline | 25 | 4 |
|  | 12.5 | 3 |
| 9-Chloro-s-triazolo(4,3-a)quinoline | 25 | 4+ |

TABLE 5:-continued

CONTROL OF RICE BLAST, PRE-PLANT SOIL INCORPORATED APPLICATION

| Compound | Rate of Application of Compound in Pounds per Acre | Disease Rating |
|---|---|---|
| 1-Methyl-s-triazolo(4,3-a)quinoline | 12.5 | 3+ |
|  | 25 | 4+ |
|  | 12.5 | 3− |
| 9-Chloro-4,5-dihydro-s-triazolo(4,3-a)-quinoline | 25 | 5 |
|  | 12.5 | 4+ |

EXAMPLES 121–125:

Various of the triazoloquinoline compounds to be employed in accordance with the present invention were evaluated for control of rice blast (*Piricularia oryzae*) when applied to the surface of water-saturated soil in which rice was growing.

Rice (variety, Nato) was seeded in 4-inch round pots having no drainage holes. The soil was maintained in water-saturated condition throughout the test which was conducted under greenhouse conditions.

About 14 days after seeding, the seedlings were treated. Treatment was made by pouring onto the surface of soil in each pot a treating solution prepared as described in Examples 117–120. On the third day following treatment, the plants were inoculated with a pathogen suspension prepared as described in Examples 78–116 and placed in a moist chamber at 18°C. for 48 hours. The plants were then returned to normal greenhouse conditions and held for 5 days, at which time they were examined for the presence, and if present, degree of severity, of symptoms of rice blast.

Three replicates were run for each test. A control was also conducted for each test; the control consisted of usage of an aqueous solution containing 0.5 percent of ethanol, only. The results of the evaluations are reported in the following table. Control pots uniformly showed extensive rice blast disease symptoms.

triazoloquinoline compound to be evaluated was dissolved in ethanol and diluted with water containing 0.1 percent of polyoxyethylene sorbitan monolaurate to obtain treating solutions containing the subject compound in various concentrations. All solutions uniformly contained 0.5 percent of ethanol and approximately 0.1 percent of the polyoxyethylene sorbitan monolaurate.

Twenty milliliters of each solution were placed in a separate 125-milliliter Erlenmeyer flask and 20 cc. (about 12.5 grams) of rice seed added (variety, Nato). Each flask was stoppered and shaken for 48 hours, at which time the rice was drained and rinsed with tap water.

The treated seed was thereafter planted in 4-inch square pots and held under typical greenhouse conditions. When the emerging rice seedlings had reached a height of 3 to 4 inches (about fourteen days after seeding) they were inoculated with a fungal suspension of *Piricularia oryzae* (rice blast) prepared as in Examples 78–116. The plants were then incubated in a moist chamber at 18°C. for 48 hours, after which they were returned to the greenhouse and held for about 5 days. They were then evaluated for disease severity, utilizing the rating system reported in preceding examples.

In each test, there were three replicates and two controls: (1) water containing 0.5 percent ethanol and 0.1 percent of polyoxyethylene sorbitan monolaurate;

TABLE 6:

CONTROL OF RICE BLAST, SOIL SURFACE APPLICATION

| Compound | Rate of Application of Compound in Pounds/Acre | Disease Rating |
|---|---|---|
| 4,5-Dihydro-s-triazolo(4,3-a)quinoline | 25 | 4+ |
|  | 12.5 | 4 |
|  | 6.25 | 4− |
| 9-Chloro-s-triazolo(4,3-a)quinoline | 25 | 4− |
|  | 12.5 | 4− |
|  | 6.25 | 3+ |
| 1-Trifluoromethyl-s-triazolo(4,3-a)-quinoline | 25 | 4+ |
|  | 12.5 | 2 |
| 9-Chloro-4,5-dihydro-s-triazolo(4,3-a)-quinoline | 25 | 5* |
|  | 12.5 | 5 |
|  | 6.25 | 4+ |
|  | 5 | 4+ |
|  | 2.5 | 4− |
|  | 1.25 | 3− |
| 1-Chloro-s-triazolo(4,3-a)quinoline | 25 | 4+ |
|  | 12.5 | 4− |
|  | 6.25 | 3− |

*Substantial phytotoxicity observed.

EXAMPLES 126–130:

Various of the present triazoloquinoline compounds were evaluated for their efficacy in controlling rice blast when applied to the rice seed. The respective and (2) plain water. In the control plots, there were extensive symptoms of rice blast.

The results of these evaluations were as set forth in the following tables.

TABLE 7:

| Compound | SEED-SOAK EVALUATIONS Concentration of Compound in Treating Solution, in ppm. | Disease Rating |
| --- | --- | --- |
| 4,5-Dihydro-s-triazolo(4,3-a)quinoline | 1000 | 4 |
|  | 500 | 3+ |
|  | 250 | 3– |
| 4,5-Dihydro-9-methyl-s-triazolo(4,3-a)-quinoline | 1000 | 4+ |
|  | 500 | 4– |
|  | 250 | 3– |
| 9-Chloro-s-triazolo(4,3-a)quinoline | 1000 | 4+ |
|  | 500 | 4– |
|  | 250 | 3+ |
| 9-Chloro-4,5-dihydro-s-triazolo(4,3-a)-quinoline | 1000 | 4+ |
|  | 500 | 4– |
|  | 250 | 3 |
| 1-Chloro-s-triazolo(4,3-a)quinoline | 1000 | 4 |
|  | 500 | 3 |
|  | 250 | 3– |

As discussed hereinabove in detail, the compounds to be employed in the practice of the present invention are synthesized from 2-hydrazinoquinoline and 3,4-dihydro-2-hydrazinoquinoline starting materials. These compounds are defined as being of the following respective formulae, wherein $R^1$ and $R^3$ have the meanings set forth above.

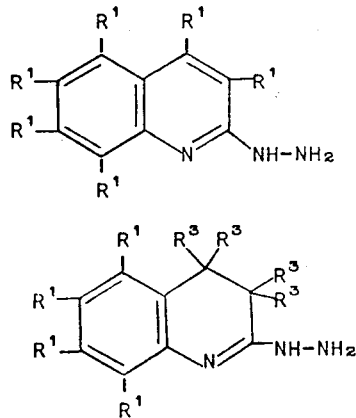

Many of these 2-hydrazinoquinoline and 3,4-dihydro-2-hydrazinoquinoline compounds are themselves prepared in known procedures, as, for example, by reaction of 2-chloroquinoline with hydrazine. However, in a preferred synthetic method for the preparation of the 3,4-dihydro-2-hydrazinoquinolines, hydrazine is reacted with a 2-thio-3,4-dihydrocarbostyril:

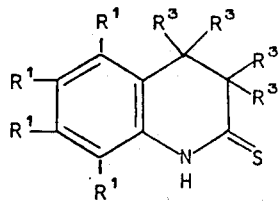

The reaction is conveniently conducted in a liquid reaction medium; water, the loweralkanols, and ether are suitable. The reaction proceeds under a wide variety of reaction temperatures, but is preferably conducted at room temperature. The hydrazine can be supplied as the hydrate or as a salt of hydrazine. The reaction consumes the reactants in equimolecular amounts, but the reaction is conveniently conducted with excess hyrazine. Separation, and, if desired, purification, are conducted in conventional procedures.

In all the foregoing, the 2-hydrazinoquinoline and 3,4-dihydro-2-hydrazinoquinoline compounds have been described as being of uniformly one structure. However, it is believed that the compounds actually exist as a tautomer:

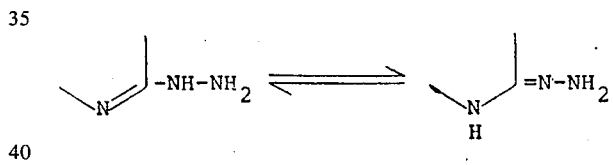

and such a tautomer can be used in the synthesis of the compounds of Formulae I and II.

We claim:
1. A compound selected from the group consisting of 4,5-dihydro-s-triazolo(4,3-a)quinoline, 4,5-dihydro-1-methyl-s-triazolo(4,3-a)quinoline, 9-chloro-4,5-dihydro-s-triazolo(4,3-a)quinoline, and 4,5-dihydro-9-methyl-s-triazolo(4,3-a)quinoline.
2. The compound of claim 1 which is 4,5-dihydro-s-triazolo(4,3-a)quinoline.
3. The compound of claim 1 which is 4,5-dihydro-1-methyl-s-triazolo(4,3-a)quinoline.
4. The compound of claim 1 which is 9-chloro-4,5-dihydro-s-triazolo(4,3-a)quinoline.
5. The compound of claim 1 which is 4,5-dihydro-9-methyl-s-triazolo(4,3-a)quinoline.

* * * * *